United States Patent [19]
Webb

[11] Patent Number: 5,304,158
[45] Date of Patent: Apr. 19, 1994

[54] DISPOSABLE DIAPER SYSTEM

[76] Inventor: Joseph A. Webb, 4650 Glen Oaks Cir., Beaumont, Tex. 77708

[21] Appl. No.: 5,745

[22] Filed: Jan. 19, 1993

[51] Int. Cl.⁵ .............................................. A61F 13/16
[52] U.S. Cl. .................................................... 604/385.1
[58] Field of Search ..................................... 604/385.1

[56] References Cited

U.S. PATENT DOCUMENTS

| | | |
|---|---|---|
| 3,865,110 | 2/1975 | Traverse . |
| 4,221,221 | 9/1980 | Ehrlich . |
| 4,702,378 | 10/1987 | Finkel et al. . |
| 4,738,678 | 4/1988 | Paulis ................................ 604/385.1 |
| 4,743,240 | 5/1988 | Powell . |
| 4,790,840 | 12/1988 | Cortina ............................ 604/385.1 |
| 4,917,693 | 4/1990 | Terry . |
| 4,923,455 | 5/1990 | Dean et al. ....................... 604/385.1 |
| 4,931,052 | 6/1990 | Feldman . |
| 4,964,859 | 11/1990 | Feldman . |
| 4,968,311 | 11/1990 | Chickering et al. ............. 604/385.1 |
| 5,141,505 | 8/1992 | Barrett .............................. 604/385.1 |

Primary Examiner—Randall L. Green
Assistant Examiner—Elizabeth M. Burke
Attorney, Agent, or Firm—Thomas R. Lampe

[57] ABSTRACT

A disposable diaper system including a diaper body having a pouch, a changing pad within the pouch which can be removed therefrom and form a surface shield extending away from the diaper body, containers connected to the changing pad for containing personal care products, and a disinfectant connected to the changing pad. The soiled diaper is placed in the pouch and wrapped in the changing pad for disinfectant and disposal purposes.

3 Claims, 1 Drawing Sheet

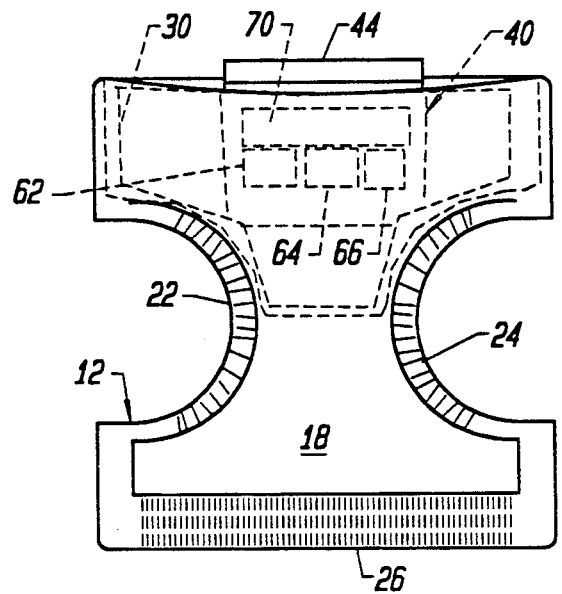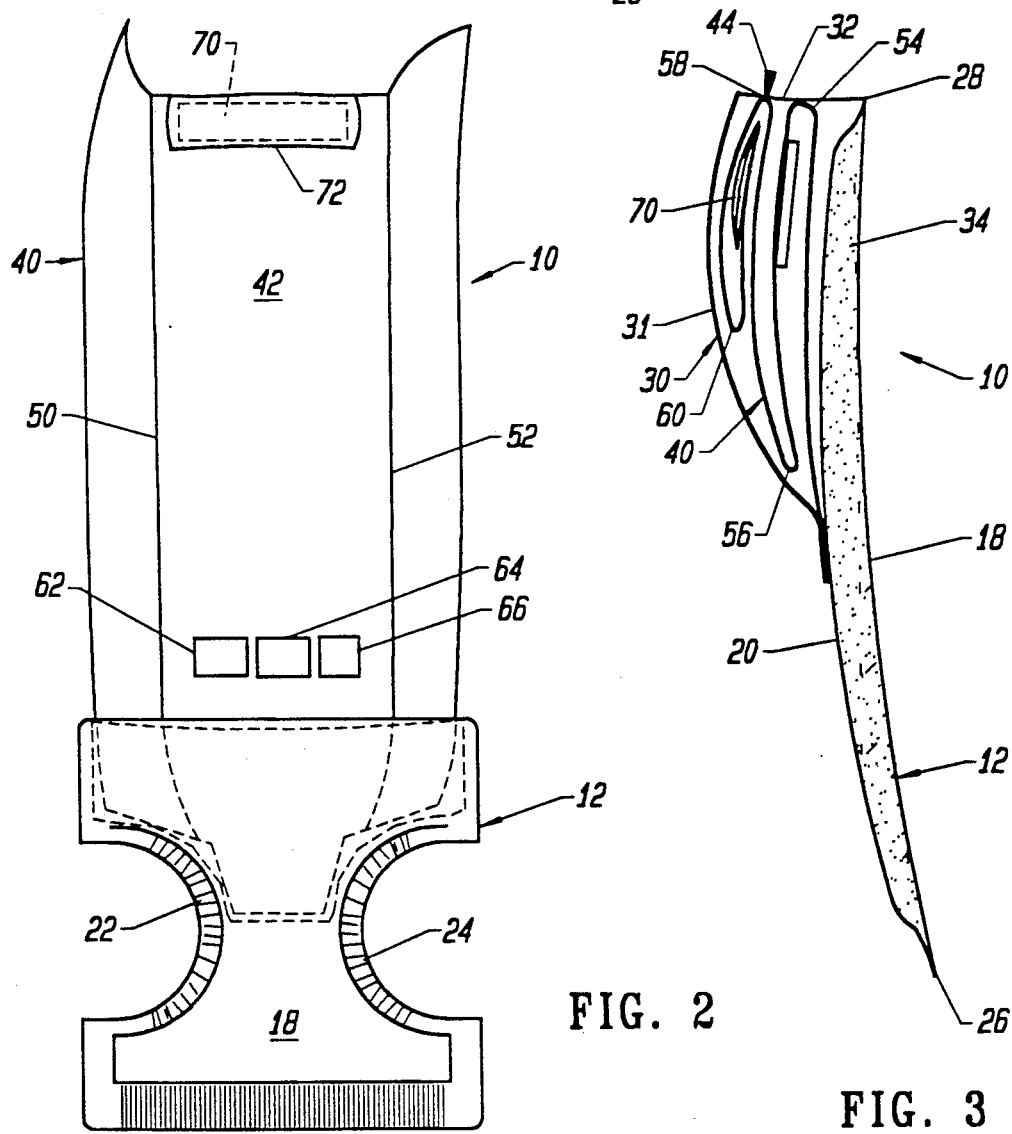

DISPOSABLE DIAPER SYSTEM

TECHNICAL FIELD

This invention relates to the diaper art. More particularly, the invention pertains to a disposable diaper system which includes a disposable diaper, a changing pad connected thereto and a container arrangement for containing personal care products and a disinfectant agent.

BACKGROUND ART

The prior art discloses a number of disposable diaper devices incorporating packets or containers containing baby care products such as lotions or the like. Examples of such devices are disclosed in U.S. Pat. No. 4,221,221, issued Sep. 9, 1980, and U.S. Pat. No. 4,743,240, issued May 10, 1988. The diaper construction shown in U.S. Pat. No. 4,743,240 also teaches the general ideal of integrally forming a bag with the diaper to be inverted and encapsulate a soiled diaper.

U.S. Pat. No. 4,964,859, issued Oct. 23, 1990, discloses a disposable diaper with an integral changing pad. The pad, which also operates as a disposable container means, is in the form of a liquid impermeable membrane 22 which is positioned over the diaper, when unfolded, to provide support for the baby.

Other patents disclosing various types of diaper constructions are: U.S. Pat. No. 4,702,378 issued Oct. 27, 1987, U.S. Pat. No. 4,790,840, issued Dec. 13, 1988, U.S. Pat. No. 4,917,693, issued Apr. 17, 1990, U.S. Pat. No. 3,865,110, issued Feb. 11, 1975, and U.S. Pat. No. 4,931,052, issued Jun. 5, 1990, the latter being closely related to U.S. Pat. No. 4,964,859, noted above.

DISCLOSURE OF INVENTION

The present invention relates to a disposable diaper system including a diaper body having front and back portions and defining a pouch having an interior and an opening communicating with the pouch interior.

A changing pad is connected to the diaper body and selectively manually movable relative to the diaper body between a first position wherein the changing pad is substantially disposed within the pouch interior to a second position wherein the changing pad is substantially removed from the pouch interior and presents a planar surface shield extending away from the diaper body.

The disposable diaper system additionally comprises a container connected to the changing pad for containing personal care products. The container is located within the pouch interior when the changing pad is in the first position and located externally of the pouch interior on the support surface when the changing pad is in the second position whereby the personal care product may be readily accessed.

A significant feature of the present invention resides in the fact that the disposable diaper system includes disinfectant means connected to the changing pad. The disinfectant means is located within the pouch interior when the changing pad is in the first position and located externally of the pouch interior when the changing pad is in the second position.

Other features, advantages, and objects of the present invention will become apparent with reference to the following description and accompanying drawings.

BRIEF DESCRIPTION OF DRAWINGS

FIG. 1 is a top plan view of the disposable diaper system of the present invention, with the changing pad and related structure disposed within a pouch formed in the diaper body;

FIG. 2 is a view similar to FIG. 1, but illustrating the changing pad and related structure, including personal care product containers and disinfectant means removed from the pouch and in position for use; and FIG. 3 is a side view of the disposable diaper system with the changing pad and related structure in the pouch, showing the positions assumed thereby prior to use.

BEST MODE FOR CARRYING OUT THE INVENTION

Referring now to the drawings, a diaper system constructed in accordance with the teachings of the present invention is designated generally by reference numeral 10. The system includes a diaper body 12 of multi-laminate construction having opposed flexible diaper front wall 18 and rear wall 20 which are heat sealed or otherwise secured together in face-to-face relationship.

Such sealing is accomplished along the entirety of side edges 22, 24, front edge 26, and back edge 28. Rear wall 20 is preferably formed of plastic sheeting as is conventional, and heat sealed to rear wall 20 and extending between side edges 22 and 24 is a plastic sheet 30 forming a pouch 31 having an interior at the back of the diaper body. The pouch is open at one end thereof (the upper end as viewed in FIG. 3) and is otherwise sealed about the periphery thereof to rear wall 20.

The pouch opening 32 is in communication with the interior of the pouch. If desired, the diaper rear wall 20 and the sheet 30 may be temporarily secured together as by means of a perforated tab or tear line (not shown) extending along the back edge 28 so that the opening 32 is not actually formed until the user exerts opposed pulling forces on the diaper rear wall 20 and sheet 30 to pull them apart.

The diaper body 12 also includes suitable batting or other absorbent material 34 between diaper walls 18 and 20.

Disposed within the pouch 31 defined by diaper wall 20 and sheet 30 is a changing pad 40 which is preferably formed of a suitable liquid-proof material such as plastic sheeting. With specific reference to FIG. 2, the changing pad 40 is shown as having been withdrawn from within the confines of the pouch 31. It will be appreciated that the changing pad 40, when removed from the pouch, will be unfolded to present a planar surface shield 42, extending away from the diaper body 12. Since virtually the entire changing pad is located away from the diaper body, a baby or small child can be positioned on a clean surface spaced from the soiled diaper body. A pull tab 44 affixed to the changing pad 40 can be utilized to pull the changing pad 40 from within the confines of the pouch. The changing pad is heat sealed or otherwise secured at one end thereof (the lowermost end as viewed in FIG. 2) between rear wall 20 and sheet 30.

The changing pad 40 is folded both along longitudinal fold lines and lateral fold lines when within the pouch. For example, FIG. 2 shows longitudinal fold lines 50, 52 and FIG. 3 shows lateral fold lines 54, 56, 58, and 60.

Attached to the changing pad 40 are containers 62, 64 and 66, each of which contains a personal care product. Examples of such products are lotions, powders, oils, ointments, and wipes. When the changing pad 40 is in its extended and open position with the side panels defined by fold lines 50, 52 unfolded, straightened out, and in alignment with the rest of the changing pad, these personal care products will be conveniently presented for use by the care giver.

An important feature of the present invention resides in the fact that disinfectant means is connected to the changing pad. The disinfectant, in the arrangement shown, and prior to removal of the changing pad from the pouch, is located within the folds of the changing pad, between the outer plastic wall or sheet 30 forming the pouch and the rear wall 20 of the diaper body. A particularly suitable disinfectant is chlorine in the form of chlorine impregnated hydrophilic strip 70 which is attached to the distal end of the changing pad 40. A removable cover 72 may be disposed over the strip 70 until exposure of the strip is secured. Releasable adhesive may be employed to secure the cover to the changing pad. It is important to note that the disinfectant, when the changing pad is in the pouch, prior to removal, is kept from the baby's body by numerous layers of the plastic pad.

After the baby or small child has been ministered to by the care giver and removed from the changing pad, the diaper body is folded back upon itself and inserted into the pouch 31 formed by the diaper body rear flexible wall 20 and sheet 30 through the afore-described opening 32 communicating with the interior of the pouch. Next, disinfectant strip 70 is exposed by removing cover 72. Now the care provider inserts the strip 70 and distal end of the changing pad into the pouch. That segment of the changing pad which remains external of the pouch is then rolled about the diaper body so that a package is formed. The combination of disinfectant, pressure (from the rolling-up action), moisture from the excreta on the diaper body, and temperature generated within the confines of the pouch will activate the disinfectant to destroy or at least inhibit the spread of certain bacterial and viral entities.

I claim:

1. A disposable diaper system comprising, in combination:

a diaper body having a flexible diaper front wall and rear wall sealed together and having attached to the rear wall a plastic sheet defining a pouch having a pouch interior and an opening communicating with said pouch interior;

a changing pad connected to said diaper body at the rear wall and selectively manually movable relative to said diaper body between a first position wherein said changing pad is substantially disposed within said pouch interior to a second position wherein said changing pad is substantially removed from said pouch interior for positioning on a support surface to present a planar surface shield extending away from said diaper body, said changing pad including a flexible, substantially liquid impermeable sheet folded along a plurality of folds defining a plurality of layers in at least partial registry when the changing pad is in said first position;

at least one container connected to said flexible, substantially liquid impermeable sheet at a first predetermined location on said flexible, substantially liquid impermeable sheet for containing a personal care product, said at least one container being located within said pouch interior when said changing pad is in said first position and located externally of said pouch interior on said support surface when said changing pad is in said second position whereby the personal care product in said at least one container may be readily manually accessed when the changing pad is in said second position; and disinfectant means connected to said flexible, substantially liquid impermeable sheet at a second location on said flexible substantially liquid impermeable sheet spaced from said first location, said disinfectant means being located within said pouch interior when said changing pad is in said first position and located externally of said pouch interior when said changing pad is in said second position, a plurality of layers of said flexible, substantially liquid impervious sheet being disposed between said disinfectant means and said flexible diaper wall and between said disinfectant means and said at least one container when said changing pad is in said first position, and said disinfectant means being spaced from said diaper body a greater distance than said at least one container is spaced from the diaper body when the changing pad is in said second position, said disinfectant means for positioning in said flexible, substantially liquid impermeable sheet along with said diaper body when the diaper body is wrapped in said flexible, substantially liquid impermeable sheet for disposal whereby the disinfectant means disinfectant the diaper when wrapped.

2. The disposable diaper system according to claim 1 wherein said disinfectant means comprises a chlorine impregnated hydrophilic strip.

3. The disposable diaper system according to claim 2 wherein said disinfectant strip at least partially comprises bleach.

* * * * *